US006375638B2

(12) United States Patent
Nason et al.

(10) Patent No.: US 6,375,638 B2
(45) Date of Patent: *Apr. 23, 2002

(54) INCREMENTAL MOTION PUMP MECHANISMS POWERED BY SHAPE MEMORY ALLOY WIRE OR THE LIKE

(75) Inventors: Clyde Nason, Valencia; William H. Stutz, Jr., Eagle Rock, both of CA (US)

(73) Assignee: Medtronic MiniMed, Inc., Northridge, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/249,666

(22) Filed: Feb. 12, 1999

(51) Int. Cl.⁷ .............................................. A61M 37/00
(52) U.S. Cl. ...................... 604/132; 604/131; 604/151; 604/153
(58) Field of Search ................................ 604/131, 154, 604/151, 155, 134, 135, 152, 133, 530, 531, 153; 606/78, 105

(56) References Cited

U.S. PATENT DOCUMENTS

| | | | |
|---|---|---|---|
| 5,178,609 A | | 1/1993 | Ishikawa |
| 5,626,581 A | * | 5/1997 | Staehlin et al. ................ 606/63 |
| 5,816,306 A | * | 10/1998 | Giacomel ....................... 160/6 |
| 5,919,167 A | * | 7/1999 | Mulhauser et al. .......... 604/131 |
| 5,961,496 A | | 10/1999 | Nielsen et al. |
| 6,033,412 A | * | 3/2000 | Losken et al. ............... 606/105 |
| 6,157,101 A | * | 12/2000 | Ullakko ........................ 310/25 |
| 6,200,317 B1 | * | 3/2001 | Aalsma et al. ................ 606/62 |

OTHER PUBLICATIONS

"Shape Memory Alloy Inchworm Actuator" by Nannette M. Schnabel; Mechanical Engineering Department California Polytechnic State University San Luis Obispo 1989; 39 pages, Jun. 14, 1989.*

"Shape Memory Alloy Inchworm Actuator" by Nannette M. Schnabel; Jun. 14, 1989; Mechanical Engineering Department California Polytechnic State University San Luis Obispo 1989; 39 pages.

* cited by examiner

Primary Examiner—Glenn K. Dawson
Assistant Examiner—Jennifer Maynard
(74) Attorney, Agent, or Firm—Medtronic MiniMed, Inc.

(57) ABSTRACT

A drive mechanism for a medication delivery device includes a force receiving member, a force applying member and a shape memory alloy (SMA) actuator. The force applying member is operatively coupled to the force receiving member to move the force receiving member to a different position relative to the force applying member. The shape memory alloy actuator is formed from a shape memory alloy material and is operatively coupled to the force applying member. The shape memory alloy actuator is heat activated to distort the shape memory actuator from a first shape to a second shape to activate the force applying member to act upon the force receiving member to move the force receiving member to a different position relative to the force applying member. Also, the shape memory alloy actuator is returned to the first shape from the second shape after the force receiving member is moved to a different position relative to the force applying member. In addition, the shape memory alloy actuator may be activated by applying and removing an electrical current to the shape memory element. For example, the drive mechanism may further include a power source coupled to the shape memory actuator to provide the electric current to the shape memory actuator. In addition, the shape memory actuator may be formed from Nitinol material, such as a wire.

26 Claims, 7 Drawing Sheets

US 6,375,638 B2

INCREMENTAL MOTION PUMP MECHANISMS POWERED BY SHAPE MEMORY ALLOY WIRE OR THE LIKE

FIELD OF THE INVENTION

This invention relates to drive mechanisms for medical devices and, in particular embodiments, to a drive mechanism for a medication infusion pump that utilizes shape memory alloy wire to activate the drive motion.

BACKGROUND OF THE INVENTION

Traditionally, drive mechanisms for medication infusion pumps have used a motor that rotates a lead screw that is connected to a carriage, and the carriage is advanced by rotation of the lead screw. For example, as the motor rotates the threads of the lead screw, corresponding threads on the carriage that are engaged with the lead screw threads, advance the carriage forward along the lead screw. Generally, the carriage is connected to a nut, or other engagement member, that is connected to a piston in a medication cartridge, which is advanced with the carriage to dispense medication through a catheter.

However, a drawback to lead screw mechanisms is that they require a complicated motor assembly and drive parts, making them costly to produce. In addition, the lead screw and drive motor contribute to a substantial portion of the weight and volume in a medical infusion pump.

SUMMARY OF THE DISCLOSURE

It is an object of an embodiment of the present invention to provide an improved drive mechanism for a medication infusion pump, which obviates for practical purposes, the above mentioned limitations.

According to an embodiment of the invention, a drive mechanism for a medication delivery device includes a force receiving member, a force applying member and a shape memory actuator. The force applying member is operatively coupled to the force receiving member to cause relative movement to occur between the force receiving member and the force applying member so that the force receiving member is in a different position relative to the force applying member. The shape memory actuator is formed from a shape memory material and is operatively coupled to the force applying member. Preferably, the shape memory actuator is heat activated to distort the shape memory actuator from a first shape to a second shape to activate the force applying member to act upon the force receiving member to cause the relative movement between the force applying member and the force receiving member so that the force receiving member is in the different position relative to the force applying member. Also, the shape memory actuator is returned to the first shape from the second shape after the force receiving member is in the different position relative to the force applying member. In particular embodiments, the force applying member is stationary and the force receiving member is moved by the force applying member. In other embodiments, the force receiving member remains stationary and the force applying member is moved relative to the force receiving member. In preferred embodiments, the shape memory actuator is activated by applying and removing an electrical current to the shape memory element. For example, the drive mechanism may further include a power source coupled to the shape memory actuator to provide the electrical current to the shape memory actuator. Preferably, the preferred the shape memory actuator is formed from Nitinol material, with the preferred structure being a wire. In some embodiments, the drive mechanism utilizes less than three shape memory actuators, three force receiving members and/or three force applying members. In still other embodiments, the drive mechanism utilizes less than three shape memory actuators.

In a first embodiment of the present invention, the force receiving member is a guide and the force applying member is a carriage assembly. For instance, the guide is a shaft and the carriage assembly includes at least one pawl that is actuated to incrementally move the carriage assembly relative to the shaft. In further embodiments, the carriage assembly includes at least one pawl, a lever and a cam surface on one end of the lever, and the shape memory actuator is coupled to another end of the lever and actuated to move the cam surface of the lever against the at least one pawl to incrementally move the carriage assembly relative to the shaft. In another embodiment, the force receiving member is a gear, and the different position of the gear relative to the force applying member is an angular rotation. For example, the force applying member is a wire pawl that includes the shape memory actuator to pull upon the gear to cause the angular rotation. Alternatively, the force applying member is a bar that includes the shape memory actuator to push upon the gear to cause the angular rotation.

In another embodiment, the drive mechanism includes a guide, a carriage member and a shape memory actuator. The carriage member moves relative to the guide. The shape memory actuator is formed from a shape memory material and is operatively coupled to the carriage member. In addition, the shape memory actuator is activated to distort the shape memory actuator from a first shape to a second shape to move the carriage member relative to the guide. Further, the shape memory actuator is returned to the first shape from the second shape after the carriage has moved relative to the guide.

In further embodiment of the present invention, a drive mechanism for a medication delivery device includes a shaft, a carriage and a shape memory element. The carriage is coupled to the shaft to move relative to the shaft. The carriage includes a first pawl, a first resilient member, a second pawl and a second resilient member. The first pawl has a first end and a second end with a first bore. The first bore defines an opening between the first and second ends, and the edges of the first bore grasp the shaft when the first pawl is tilted. The first resilient member is coupled between the carriage and the first pawl to bias the first pawl to a first position relative to the shaft. The second pawl has a first end and a second end with a second bore. The second bore defines an opening between the first and second ends, and the edges of the second bore grasp the shaft when the second pawl is tilted. The second resilient member is coupled between the carriage and the second pawl to bias the second pawl to resist relative rearward movement of the carriage. The shape memory element activates the first pawl to move between the first position and a second position to move the carriage relatively forward, as the shaft is grasped by the edges of the first bore, when the first pawl is moved from the first position to the second position. The first resilient member is used to move the first pawl back to the first position after the carriage has moved relative to the shaft.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
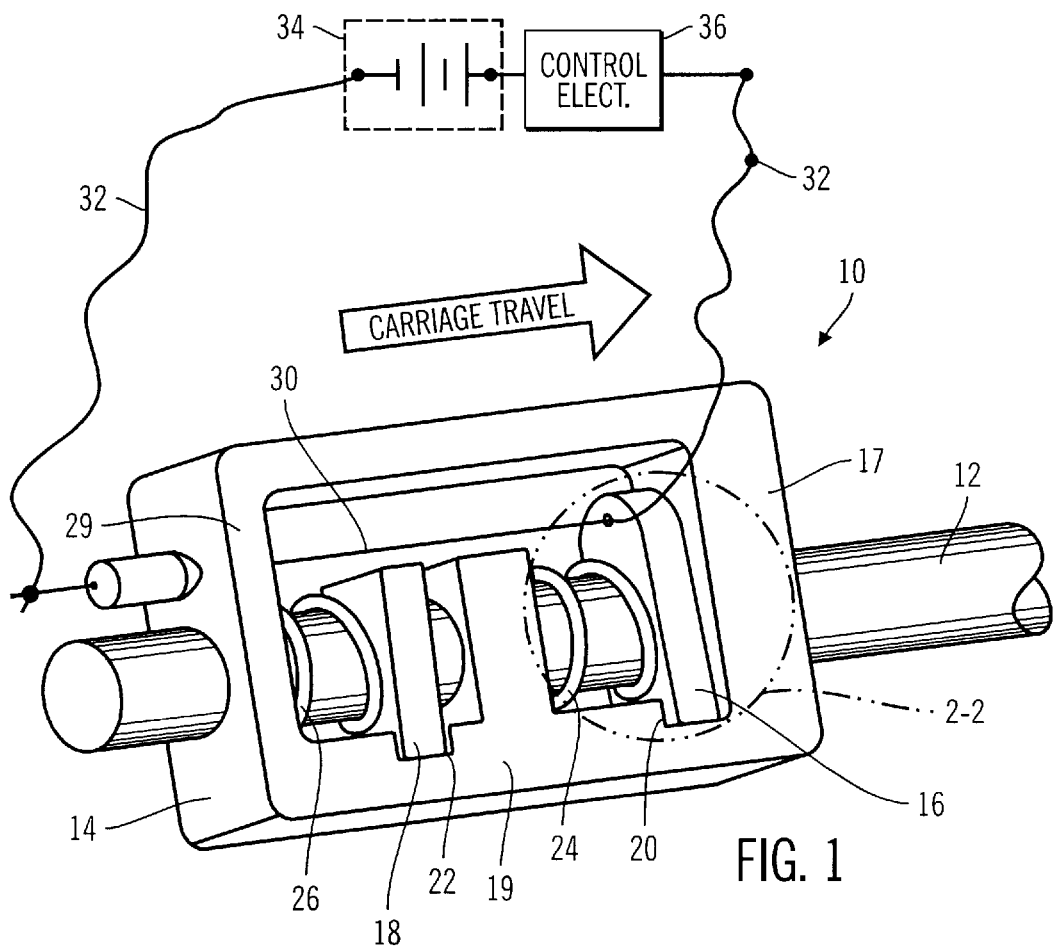
FIG. 1 is a partial perspective view of a carriage assembly and stationary shaft for a drive mechanism in accordance with a first embodiment of the present invention.

As shown in the drawings for purposes of illustration, the invention is embodied in a drive mechanism for a medication infusion pump. In preferred embodiments of the present invention, shape memory alloy wire, or the like, is used to activate an incremental motion drive mechanism for pumping liquids, such as medications, drugs, vitamins, vaccines, peptides or the like. However, it will be recognized that further embodiments of the invention may be used in other devices that require compact and accurate drive mechanisms. In addition, other shape altering materials, such as piezo-electric materials, or the like, may be used.

Preferred embodiments of the present invention utilize the shape memory material with the principle of an "inching" type motion, which is similar in some aspects to the friction type motion used in car jacks and "squeeze grip" types of woodworking clamps. However, instead of hand action, these embodiments use shape memory material, such as "Nitinol" shape memory alloy wire, or the like, and a small low voltage battery to power the device and activate the inching motion. In alternative embodiments, shape memory material structures, other than wire, such as sheets, bars, plates, rods, laminates, or the like, may be used. In addition, other shape memory alloys, or materials may be used. Relative simplicity and low cost make these types of drive mechanisms suitable for very inexpensive or disposable pumps.

Figure 2:
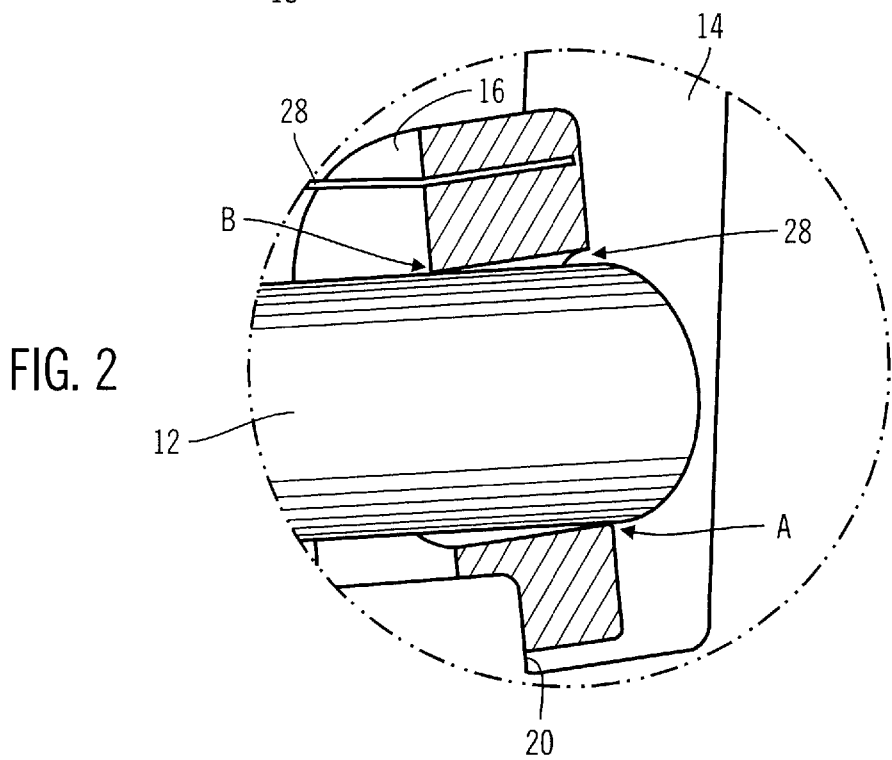
FIG. 2 is an enlarged, partial cross-sectional diagram of the drive mechanism as shown within the dashed circle 2—2 in FIG. 1.

FIGS. 1 and 2 illustrate a drive mechanism 10 in accordance with a first embodiment of the present invention. The drive mechanism includes a stationary shaft 12 and a carriage assembly 14 that travels along the stationary shaft 12.

In preferred embodiments, the stationary shaft 12 is a metal rod having a smooth surface. However, in alternative embodiments, the metal rod may be formed out of other materials, such as glass, ceramics, plastics or the like. In addition, the round metal rod may be formed with other cross-section shapes, such as rectangles, squares, triangles or the like, and the surface may be roughened or include teeth to facilitate movement of the carriage assembly 14. In other alternative embodiments, the rod may be replaced with a track, guide, recessed groove or the like. In still other alternative embodiments, the carriage assembly 14 may be fixed (or stationary) to a housing and the shaft may be moved (rather than being stationary) by the carriage assembly to depress a plunger (not shown) or the like.

In preferred embodiments, the carriage assembly 14 includes two pawls 16 and 18 that are used to "inch" (or incrementally move) along the stationary shaft 12. The forward pawl 16 is used to produce the forward "inching" movement of the carriage assembly 14 along the stationary shaft 12. The backstop (or anti-backtrack) pawl 18 is used to prevent (or substantially inhibit) backward movement of the carriage assembly 14 along the stationary shaft 12. Preferably, movement of the carriage assembly 14 is limited to a predetermined limit by a limit stop 20 to provide precise control over the increment of movement. In additional embodiments, the limit stop 20 may include a set screw, or the like, (not shown) to facilitate accurate adjustment of the movement of the carriage assembly 14 to refine the movement increment after assembly. As shown in FIGS. 1 and 2, preferably, the backstop pawl 18 is held loosely captive in a corresponding pivot groove 22 in a base plate 19 of the carriage assembly 14. The pivot groove 22 maintains the captive end of the backstop pawl 18 allowing it to pivot relative to the base plate 19 of the carriage assembly 14. Also, each of the pawls 16 and 18 is forwardly biased toward the direction of travel of the carriage assembly 14 by corresponding bias springs 24 and 26 to place a forward load against the pawls 16 and 18.

As shown in FIG. 2, a slight rearward canting (or tilting) of the forward pawl 16 relative to the stationary shaft 12 results in a binding condition (or contact) at points A and B between the edges of a bore 28 in the forward pawl 16 and the stationary shaft 12 that inhibits sliding motion from occurring. When the forward pawl 16 is oriented substantially perpendicular to the stationary shaft 12, the forward pawl 16 is free to slip along the stationary shaft 12. However, when the forward pawl 16 is oriented away from perpendicular, by shrinkage of the shape memory alloy wire 30, such that contact at points A and B occurs, the forward pawl 16 firmly grasps the stationary shaft 12 to inhibit relative movement between the forward pawl 16 and the stationary shaft 12. With the contact between A and B establishing an anchor point, the shape memory alloy wire 30 becomes effectively tied (or locked or connected) to the stationary shaft 12, and any further shrinkage of the shape memory alloy wire 30 can only result in the advancing (or pulling or sliding) of the carriage assembly 14 along the stationary shaft 12. The carriage assembly 14 will continue to advance (or pull or slide) until the limit stop 20 contacts the forward pawl 16.

The bias spring 26 biases the backstop pawl 18 slightly forward to prevent rearward movement of the carriage assembly 14. However, the forward motion of the carriage assembly 14 relative to the stationary shaft 12 moves the pivot groove 22, allowing the backstop pawl 18 to overcome the bias force from the bias spring 26. Overcoming the bias tends to tilt the backstop pawl 18 rearward, which allows the stationary shaft 12 to slide rearward relative to the backstop pawl 18 and the forward moving carriage assembly 14. Conversely, the backstop pawl 18 does not permit backward motion of the carriage assembly 14, since the bias spring 26 tilts the backstop pawl 18 slightly forward and any rearward motion of the carriage assembly 14 would provide additional force to the backstop pawl 18 (which would tend to tilt the backstop pawl 18 further forward) to increase the grasp of the backstop pawl 18 on the stationary shaft 12. This inhibits rearward movement of the carriage assembly 14 relative to stationary shaft 12. Using an alternating binding and sliding position of the forward pawl 16, an incremental inching motion along the stationary shaft 12 is accomplished.

In preferred embodiments, the carriage assembly 14 of the drive mechanism 10 may be returned to the starting position, by tilting both pawls 16 and 18 to a generally perpendicular orientation relative to the stationary shaft 12. In this orientation, there is sufficient clearance between the pawls 16 and 18 and the stationary shaft 12 to permit the carriage assembly 14 to be slid backwards to the starting point or home position. In preferred embodiments, when the shape memory alloy material 30 is in the lengthened condition, the forward pawl 16 is biased in the perpendicular orientation relative to the stationary shaft 12 by the bias spring 24 and the front wall 17 of the carriage assembly 14. Thus, the backstop pawl 18 is the only pawl that needs to be adjusted to permit resetting of the carriage assembly. The backstop pawl 18 could be adjusted manually, using a lever, or even another piece of shape memory alloy wire may be used to tilt the backstop pawl 18 back. It should be noted that it is preferred that the drive mechanism 10 remain inoperative until the pawls 16 and 18 are released again.

Spanning the distance between the forward pawl 16 and a back wall 29 of the carriage assembly 14 is a shape memory alloy wire 30 composed of a Nickel Titanium alloy known as Nitinol. In alternative embodiments, other shape memory alloys or materials, such as piezoelectric materials or the like may be used. Also, structures, other than wire, such as rods, bars, sheets or the like may be used. Electrically connected to each end of the shape memory alloy wire 30 are conductive wires 32 that are connected to a battery 34 and control electronics 36. Nitinol wire is preferred, due to its unique properties of temporarily shrinking in length when heated to about 70° C. above ambient temperature and then returning to its original length when cooled. Passage of a small electric current, from the battery 34 via the conductive wires 32, through the shape memory allow wire 30 is sufficient to heat the shape memory alloy wire 30. The heating shrinks the length of the shape memory alloy wire 30. For example, Nitinol wire can shrink in length by as much as 6%, but this amount of shrinkage tends to reduce the life of the Nitinol element. However, the use of different materials, structures, heating energy, or the like may be used to increase or decrease the amount of shrinkage of the shape memory alloy wire. A typical conservative shrinkage percentage is generally 3% or less.

The shrinking of the shape memory alloy wire 30 is used as a pulling motion against the forward pawl 16 to tilt it backwards to grasp the stationary shaft 12 as shown in FIG. 2, and to cause a minute forward motion of the carriage assembly 14 along the stationary shaft 12. Pulsing the current to the shape memory alloy wire 30, to incrementally heat and cool, provides a series of incremental motions that propel the carriage assembly 14 along the stationary shaft for cumulative travel that delivers liquid from a reservoir in a medication infusion pump.

Figure 3:
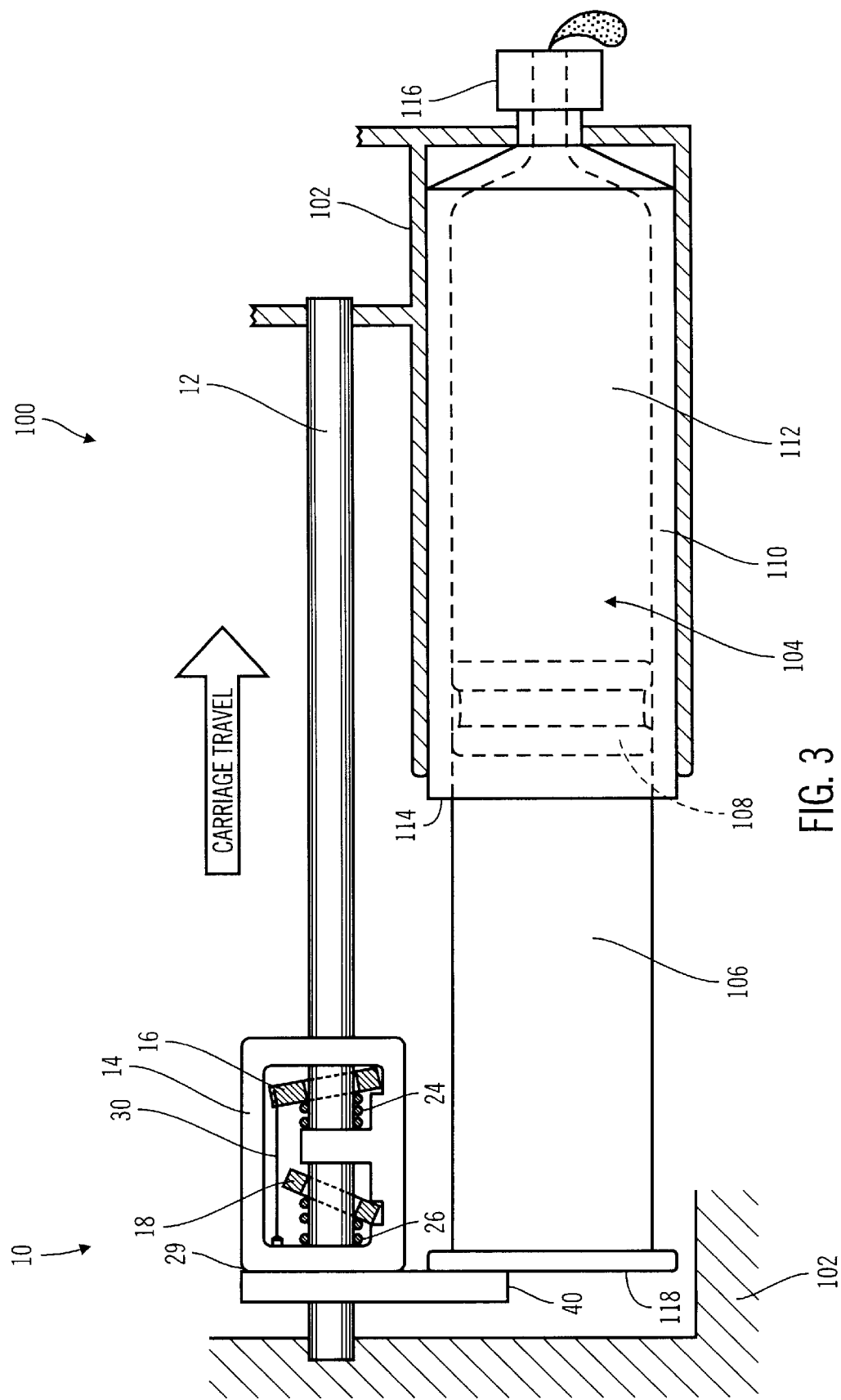
FIG. 3 is a cross-sectional diagram of a medical device using the drive mechanism shown in FIGS. 1 and 2 in accordance with an embodiment of the present invention.

FIG. 3 shows a medication infusion pump 100 in accordance with an embodiment of the present invention that utilizes the drive mechanism 10 shown in FIGS. 1 and 2. The medication infusion pump 100 includes a housing 102 for holding a reservoir 104 that is operatively coupled to the drive mechanism 10. The stationary shaft 12 is also secured to the housing 102 to provide support for the carriage assembly 14 of the drive mechanism 10. The reservoir 104 includes a plunger 106 that is coupled to a piston 108 that slides along a reservoir housing 110. The reservoir housing 110 forms a liquid chamber 112 for holding medication or the like, and has a piston receiving end 114 and an outlet end 116. The piston receiving end 114 is adapted to receive the plunger 106 and piston 108. The outlet end 116 provides an outlet for the liquid in the liquid chamber and may be configured to attach to catheters, needles, luers, infusion sets or the like. In preferred embodiments, the reservoir 104 is a disposable syringe. However, in alternative embodiments, the reservoir 104 may be a prefilled cartridge or a reusable reservoir.

In this embodiment, the carriage assembly 14 includes a drive tab 40 that is connected to the back wall 29 of the carriage assembly 14 and extends down to engage and push against an end 118 of the plunger. As the carriage assembly 14 moves along the stationary shaft 12, as discussed above, it pushes in the plunger 106 by a corresponding amount. Therefore, incremental movement of the drive mechanism 10 results in incremental advancement of the plunger 106, which pushes on the piston 108 to expel liquid from the liquid chamber 112 through the outlet end 116 of the reservoir 104. In preferred embodiments, each incremental movement of the carriage assembly is a distance that is set at the factory to provide a set amount of liquid. However, in alternative embodiments, the carriage assembly may include the capability to be adjusted to move along with different increments to provide different amounts of liquid with each movement of the carriage assembly 14.

Figure 4:
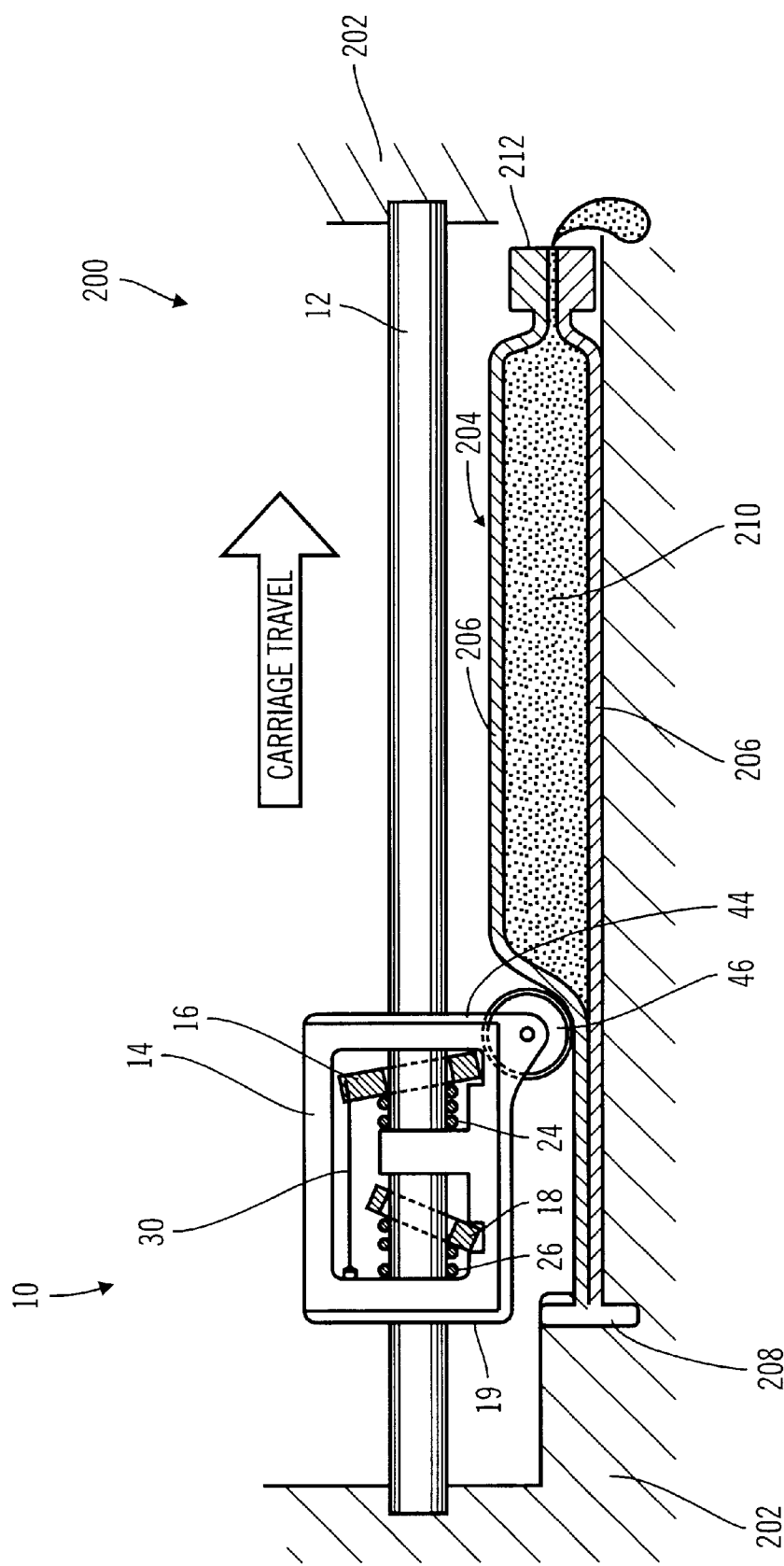
FIG. 4 is a cross-sectional diagram of a medical device using a drive mechanism in accordance with another embodiment of the present invention.

FIG. 4 shows a medication infusion pump 200 in accordance with another embodiment of the present invention that utilizes the drive mechanism 10 shown in FIGS. 1 and 2. The medication infusion pump 200 includes a housing 202 for holding a collapsible reservoir 204 that is operatively coupled to the dive mechanism 10. The stationary shaft 12 is also secured to the housing 202 to provide support for the carriage assembly 14 of the drive mechanism 10. The collapsible reservoir 204 includes flexible walls 206 that are secured together at a sealed end 208 to form a liquid chamber 210 to hold liquids such as medications or the like. The sealed end 208 is also secured to the housing 202 to prevent it from slipping. The other end of the flexible walls 206 terminate in an outlet end 212. The outlet end 212 provides an outlet for the liquid in the liquid chamber and may be configured to attach to catheters, needles, luers, infusion sets or the like. In preferred embodiments, the collapsible reservoir 204 is a disposable sack (or tube). However, in alternative embodiments, the reservoir 204 may be a prefilled sack (or tube) or a reusable, refillable reservoir.

In this embodiment, the carriage assembly 14 includes a drive hub 44 that is connected to the base plate 19 of the carriage assembly 14. The drive hub 44 also holds a rotatable wheel (or roller) 46 that extends down to engage and push against the flexible walls 206 to collapse the flexible walls 206 together. As the carriage assembly 14 moves along the stationary shaft 12, as discussed above, it collapses the flexible walls 206 as it moves over and above the collapsible reservoir 204 by a corresponding amount. In preferred embodiments, the rotatable wheel 46 provides sufficient compression to prevent the liquid in the liquid chamber 210 from passing back into the portion of the liquid chamber 210 that has been previously compressed. In other words, the motion of the carriage assembly 14 operates to squeeze the tube in a manner analogous to squeezing toothpaste from a tube. Therefore, incremental movement of the drive mechanism 10 results in incremental collapsing of the flexible walls 206, which compressed the liquid chamber 210 to expel liquid through the outlet end 212 of the collapsible reservoir 204. In preferred embodiments, each incremental movement of the carriage assembly is a distance that is set at the factory to provide a set amount of liquid. However, in alternative embodiments, the carriage assembly may include the capability to be adjusted to move along with different increments to provide different amounts of liquid with each movement of the carriage assembly 14.

Figure 5:
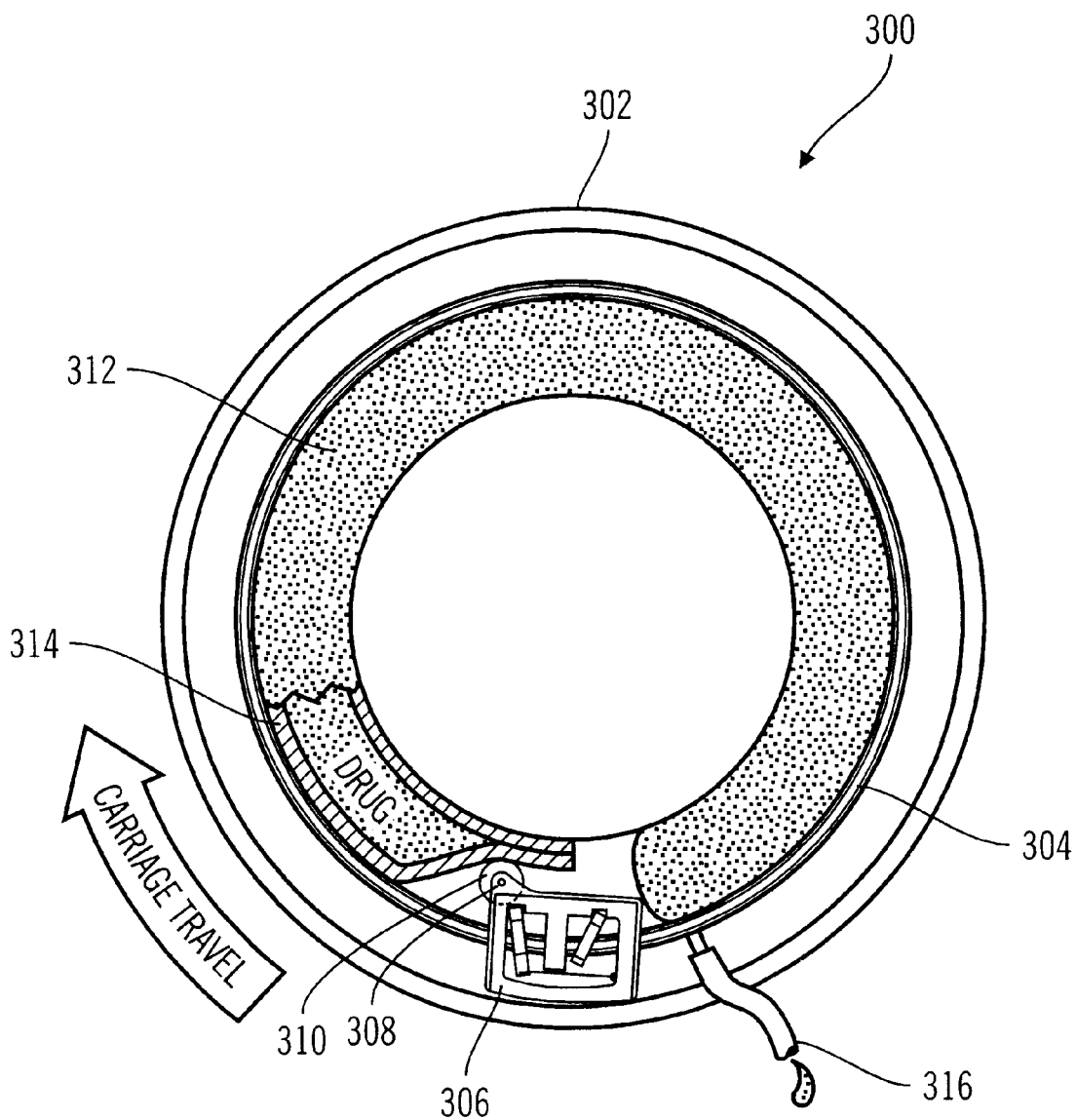
FIG. 5 is a cross-sectional diagram of a medical device using a drive mechanism in accordance with a further embodiment of the present invention.

This incremental motion can be used to move along either a straight or a curved path. For example, FIG. 5 illustrates a variation of the medical device and drive mechanism embodiment shown in FIG. 4. The medical device 300 has a housing 302 that is generally in the shape of a disk. The housing 302 contains a substantially circular stationary guide 304 and carriage assembly 306 that operate in a manner similar to that described above. The carriage assembly includes a drive hub 308 for holding a rotatable wheel 310 that bears against a collapsible fluid reservoir 312 having flexible walls 314. The carriage assembly 306 advances along the stationary guide 304 and collapses the flexible walls 314 of the liquid reservoir 312 to expel liquid, such as medication or the like, though an outlet opening 316.

Figure 7:
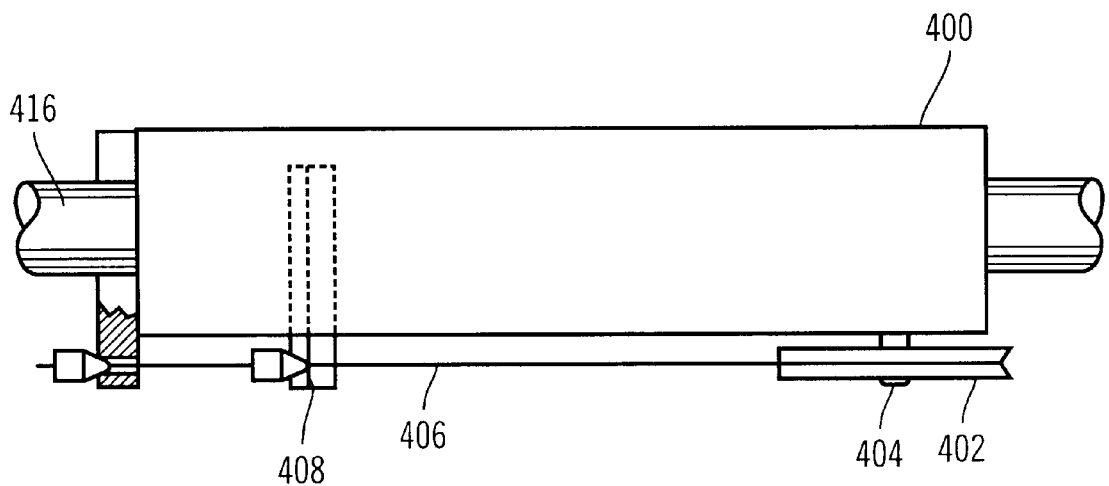
FIG. 7 is a top perspective view of a carriage assembly using a pulley arrangement to support the shape memory material in accordance with an embodiment of the present invention.
Figure 6:
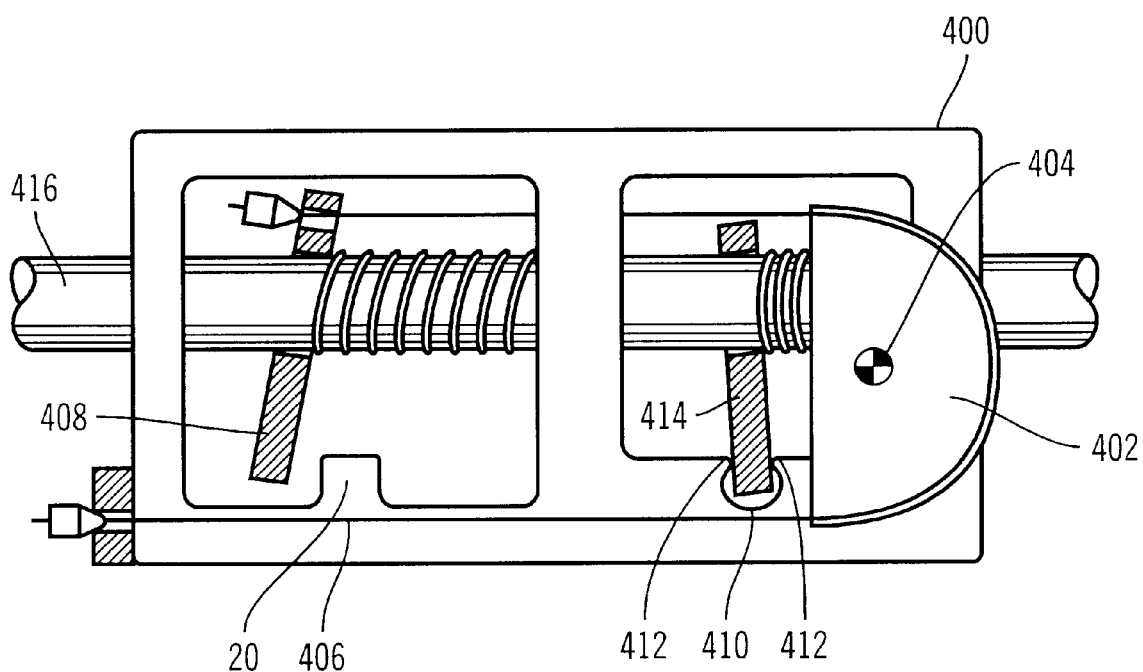
FIG. 6 is a side perspective view of a carriage assembly using a pulley arrangement to support the shape memory material in accordance with an embodiment of the present invention.

FIGS. 6 and 7 illustrate a carriage assembly 400, which is an alternative embodiment of the carriage assembly 14 shown in FIGS. 1 and 2. The carriage assembly 400 utilizes a pulley structure 402, such as a half pulley or the like, rotatably mounted on a pin 404, or the like, to support a shape memory material element 406. The use of a pulley structure 402 allows the use of a longer shape memory material element 406, as compared to the earlier embodiments, or to use the same length and have a smaller carriage assembly size. The use of a longer shape memory element 406 allows for larger contractions, which can pull the forward pawl 408 back further, reducing the number of incremental movements. Alternatively, a longer pull reduces the required shrinkage or shape change and resulting shrinkage stress on the shape memory material element 406. In other alternative embodiments, the shape memory material element 406 may be wrapped around the exterior surface of the carriage assembly 400, if the contact will not unduly stress the shape memory material element 406 and will not produce too much friction that would inhibit contraction of the shape memory material element 406. In addition, caution must be exercised that contact between the shape memory material element 406 and the carriage assembly 400 (and/or pulley structure 402) will not impede heating and/or cooling of the shape memory material element, since this can effect power requirements and activation speed (or rate of shape change) for the shape memory material element 406.

Also, as shown in FIG. 6, a modified pivot groove 410, having extended contact members 412 on either side of the pivot groove 410, is used to control the rotational motion of the second pawl 414. The extended contact members provide sufficient contact with the sides of the second pawl 414 to permit easy insertion and pivoting of the second pawl 414 within the pivot groove 410. However, use of the extended contact members 412 reduce, or eliminate, play, twisting, shifting, or the like, when the second pawl 414 is rotated during movement of the carriage assembly 400 along the shaft 416. The second pawl (or backstop pawl) 414 needs a precise pivot point to minimize lost motion, which would impede its ability to prevent backward movement. For instance, if there was a lot of lost motion, the carriage assembly could move forward one increment and back some fraction of an increment—resulting in inefficiencies and inaccuracies. Thus, the use of extended contact members provide for greater accuracy in delivery of the liquid or medication from the drive mechanism. Preferably, the extended contact members are formed as partial arcs. However, in alternative embodiments, other shapes, such as ramps, points, or the like, may be used.

Figure 8:
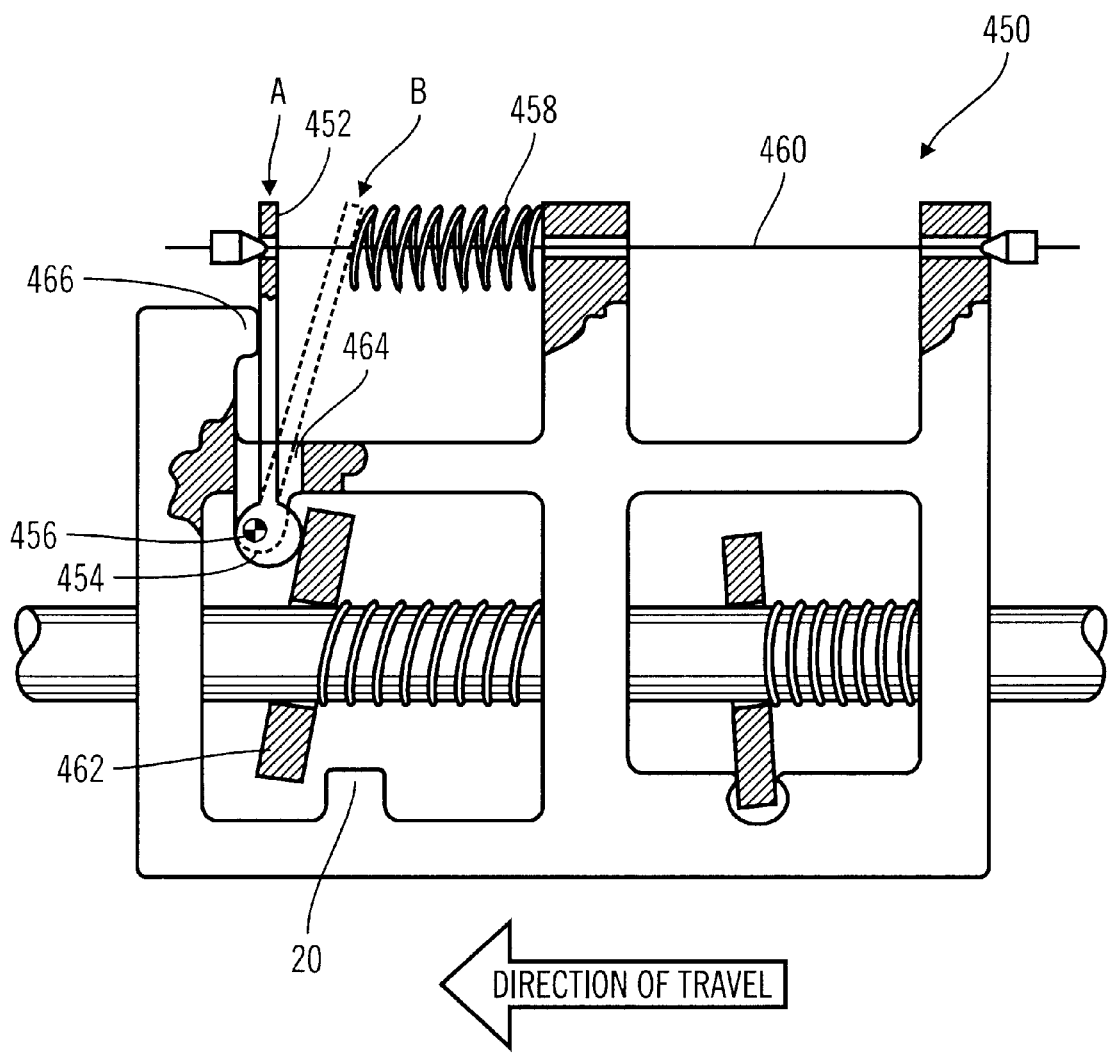
FIG. 8 is a side perspective view of a carriage assembly using a lever and cam assembly to support the shape memory material in accordance with an embodiment of the present invention.

FIG. 8 illustrates a carriage assembly 450, which is another alternative embodiment of the carriage assembly 14 shown in FIGS. 1 and 2. The carriage assembly 450 utilizes a lever 452 and a cam surface 454 attached to the lever 452 that rotates on a pivot pin 456, and a return bias spring 458 to transform a large shrinkage (or distortion) of the shape memory element 460, which would cause a large incremental movement of the carriage assembly, to a small high force incremental movement of the carriage assembly 450. Although possible to adapt the lever 452 and the cam surface 454 to provide a larger increment than the corresponding shrinkage of the shape memory element 460; this tends to stress and shorten the life of the shape memory element 460.

As illustrated the shape memory element 460 is connected to one end of the lever 452 (rather than the first pawl 462 as illustrated in FIGS. 1 and 2), which is moved from a first position (A) to a second position (B as shown in dotted lines) when the shape memory element 460 is shrunk (or distorted) by heat activation. The other end of the lever 452 passes through a lever bore 464 and is connected to the carriage assembly by the pivot pin 456 to permit rotation of the lever 452 about the pivot pin 456. The end of the lever 452 with the cam surface 456 contacts and bears against the first pawl 462 to incline the first pawl 462. As described above in the earlier embodiments, as the rotation of the cam surface 454 displaces the first pawl 462 to cause an incremental movement of the carriage assembly 450. The cam surface 454 is shaped to cause the movement of the first pawl in a way that provides more control over the setting of the movement increment of the carriage assembly 450. This allows for accurate dispensing of the fluid and makes the incremental movement of the drive mechanism less sensitive to variations in the shrinkage (or distortion) of the shape memory element 460, either from variations over time or due to variations in manufacturing. For instance, the cam surface 454 may be shaped to have an increased displacement of the first pawl 462 only up to a certain point, after which the curvature of the cam surface 454 is maintained so that further rotations of the lever 452 and cam surface 454 do not produce any further inclination (or movement) of the first pawl 462. Thus, if lever is set to provide a maximum tilt of the first pawl 462 under the minimum expected shrinkage of the shape memory element 460, any extra shrinkage due to extra heat, change in properties over time, differences in manufacturing lots, or the like, will have no effect on the incremental movement of the carriage assembly 450. Preferred embodiments also use a limit stop 20, as described above, to more accurately control the movement increment of the carriage assembly.

As illustrated the carriage assembly 450 also includes a rest stop 466 to prevent the lever 452 from rotating to far backwards as the shape memory element 460 is restored to its original shape and the lever 452 is pushed back by the bias spring 458. The use of the rest stop 466 prevents, the first pawl 462 from also inclining to far back after incremental movement of the carriage assembly 450. The rest stop 466 may also serve the purpose of minimizing stress on the shape memory element 460 due to the lever 452 being under constant tension from the bias spring 458, which could distort the shape memory element 460. In further embodiments, the rest stop 466 may include a set screw, or the like, (not shown) that permits the rest position of the lever 452 to be adjusted, calibrated and/or controlled, which would permit the incremental motion of the carriage assembly 450 to be further fine tuned after the assembly of the drive mechanism.

Figure 9:
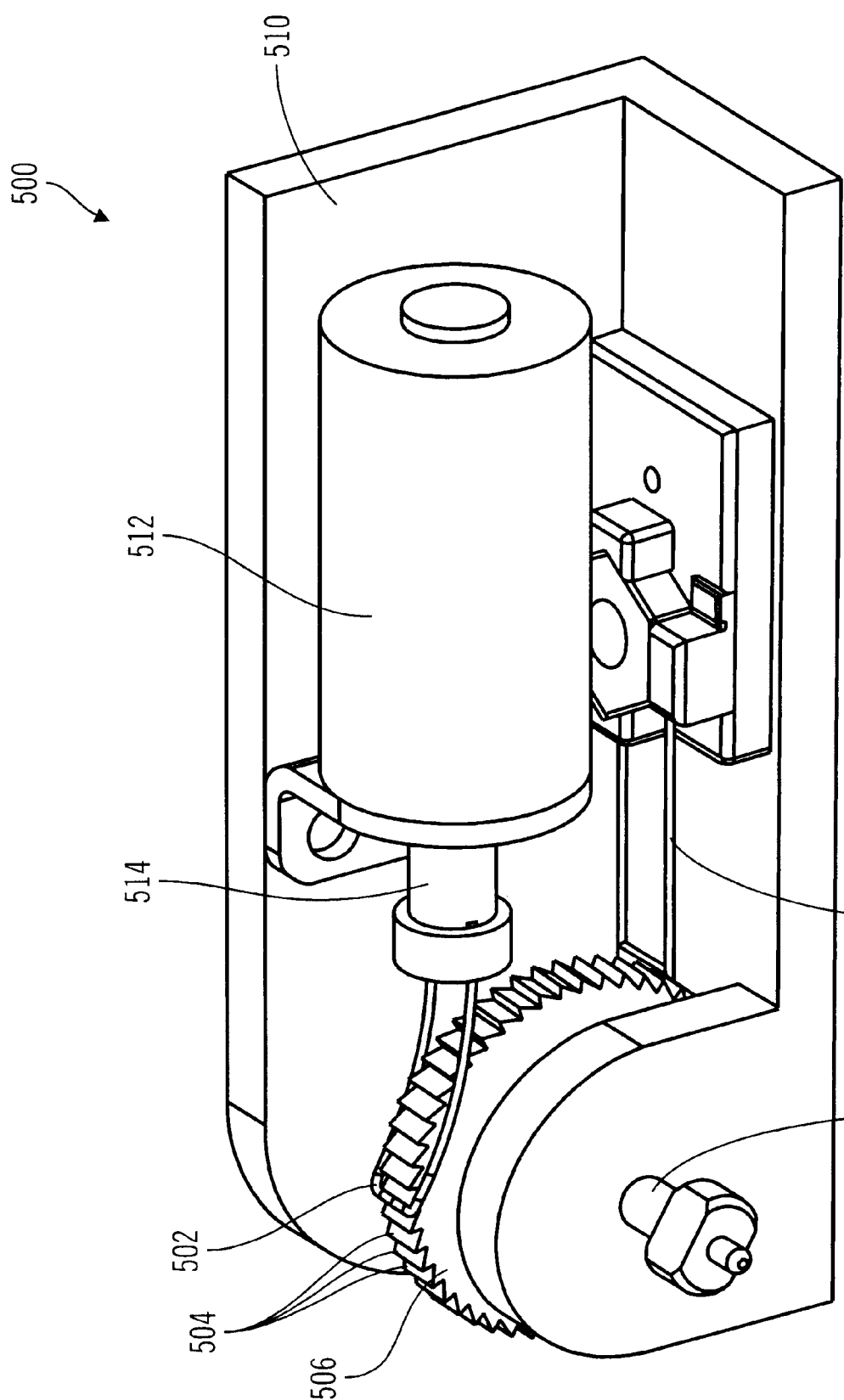
FIG. 9 is a perspective view of a drive mechanism in accordance with a second embodiment of the present invention.

As discussed above, embodiments of the present invention use shape memory materials as the actuator for the drive mechanism. However, the above-described embodiments are not the only way to use shape memory materials for actuation of a drive mechanism. For example, FIG. 9 illustrates a drive mechanism 500 in accordance with second embodiment of the present invention. The drive mechanism 500 includes a shape memory material pull 502 that is actuated to contract and pull on teeth 504 of a gear 506, which in turn rotates and/or ratchets the gear 506 to drive the medication infusion pump mechanism. After the gear 506 is rotated, the shape memory material 502 is allowed to expand and slide over the next tooth 504 on the gear 506. Preferably, the gear 506 is rotatably mounted to a pin 508 that is secured to a support housing 510. The shape memory material is activated by a power supply 512 that is connected to control electronics 514 to adjust the shape of the shape memory material 502. To keep the gear from rotating backwards, a backstop pawl 516 engages with the teeth 504 of the gear 506 in a ratchet manner. In an alternative embodiment, the shape memory material may be a bar structure, or the like, that pushes on the teeth 504 of the gear, as opposed to pulling, to rotate the gear 506 and actuate the drive mechanism 500.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A drive mechanism for a medication delivery device, the drive mechanism comprising:
 a force receiving member;
 a force applying member operatively coupled to the force receiving member to cause relative movement to occur between the force receiving member and the force applying member so that the force receiving member is in a different position relative to the force applying member; and
 a shape memory actuator formed from a shape memory material and which is operatively coupled to the force applying member, and wherein the shape memory actuator is heat activated to distort the shape memory actuator from a first shape to a second shape to activate the force applying member to act upon the force receiving member to cause the relative movement between the force applying member and the force receiving member so that the force receiving member is in the different position relative to the force applying member, and wherein the shape memory actuator is returned to the first shape from the second shape after the force receiving member is in the different position relative to the force applying member;
 wherein the force receiving member is a guide and the force applying member is a carriage assembly, and
 wherein the guide is a shaft and the carriage assembly includes at least one pawl, a lever and a cam surface on one end of the lever, and wherein the shape memory actuator is coupled to another end of the lever and actuated to move the cam surface of the lever against the at least one pawl to incrementally move the carriage assembly relative to the shaft.

2. A drive mechanism in accordance with claim 1, wherein the force applying member is stationary and the force receiving member is moved by the force applying member.

3. A drive mechanism in accordance with claim 1, wherein the force receiving member remains stationary and the force applying member is moved relative to the force receiving member.

4. A drive mechanism in accordance with claim 1, wherein the shape memory element is heat activated by applying and removing an electric current to the shape memory element.

5. A drive mechanism in accordance with claim 4, wherein the drive mechanism further includes a power source coupled to the shape memory element to provide the electric current to the shape memory element.

6. A drive mechanism in accordance with claim 4, wherein the shape memory element is formed from Nitinol material.

7. A drive mechanism in accordance with claim 6, wherein the Nitinol material is formed as a wire.

8. A drive mechanism in accordance with claim 1, wherein the drive mechanism utilizes less than three force receiving members and three force applying members.

9. A drive mechanism in accordance with claim 1, wherein the shape memory element becomes shorter when heated.

10. A drive mechanism in accordance with claim 1, wherein the shape memory element is free of coils.

11. A drive mechanism for a medication delivery device, the drive mechanism comprising:
 a force receiving member;
 a force applying member operatively coupled to the force receiving member to cause relative movement to occur between the force receiving member and the force applying member so that the force receiving member is in a different position relative to the force applying member; and
 a shape memory actuator formed from a shape memory material and which is operatively coupled to the force applying member, and wherein the shape memory actuator is heat activated to distort the shape memory actuator from a first shape to a second shape to activate the force applying member to act upon the force receiving member to cause the relative movement between the force applying member and the force receiving member so that the force receiving member is in the different position relative to the force applying member, and wherein the shape memory actuator is returned to the first shape from the second shape after the force receiving member is in the different position relative to the force applying member;
 wherein the shape memory actuator provides a pulling force when heated; and wherein the force receiving member is a gear, and wherein the different position of the gear relative to the force applying member is only an angular rotation, and wherein the force applying member is a bar formed from the shape memory actuator to push upon the gear to cause the angular rotation.

12. A drive mechanism in accordance with claim 11, wherein the shape memory actuator becomes shorter when heated.

13. A drive mechanism in accordance with claim 11, wherein the shape memory actuator is free of coils.

14. A drive mechanism for a medication delivery device, the drive mechanism comprising:
   a shaft;
   a carriage coupled to the shaft to move relative to the shaft, wherein the carriage includes:
      a first pawl having a first end and a second end with a first bore defining an opening between the first and second ends, wherein edges of the first bore grasp the shaft when the first pawl is tilted;
      a first resilient member coupled between the carriage and the first pawl to bias the first pawl to a first position relative to the shaft;
      a second pawl having a first end and a second end with a second bore defining an opening between the first and second ends, wherein edges of the second bore grasp the shaft when the second pawl is tilted;
      a second resilient member coupled between the carriage and the second pawl to bias the second pawl to resist relative rearward movement of the carriage; and
   a shape memory element to activate the first pawl to move between the first position and a second position to move the carriage relatively forward, as the shaft is grasped by the edges of the first bore, when the first pawl is moved from the first position to the second position,
   wherein the first resilient member moves the first pawl back to the first position after the carriage has moved relative to the shaft.

15. A drive mechanism in accordance with claim 14, wherein the shape memory element is activated by applying and removing an electric current to the shape memory element.

16. A drive mechanism in accordance with claim 15, wherein the drive mechanism further includes a power source coupled to the shape memory element to provide the electric current to the shape memory element.

17. A drive mechanism in accordance with claim 15, wherein the shape memory element is formed from Nitinol material.

18. A drive mechanism in accordance with claim 15, wherein the Nitinol material is formed as a wire.

19. A drive mechanism for a medication delivery device, the drive mechanism comprising:
   a force receiving member;
   a force applying member including a body and a pawl, wherein the pawl is pivotally coupled to the body, and wherein the force applying member is directly contacting the force receiving member to cause relative movement to occur between the force receiving member and the force applying member so that the force receiving member is in a different position relative to the force applying member;
   a shape memory actuator formed from a shape memory material and which is connected to the force applying member, and wherein the shape memory actuator is heat activated to distort the shape memory actuator from a first shape to a second shape to activate the force applying member to act upon the force receiving member to cause the relative movement between the force applying member and the force receiving member so that the force receiving member is in the different position relative to the force applying member, and wherein the shape memory actuator is returned to the first shape from the second shape after the force receiving member is in the different position relative to the force applying member; and
   wherein the shape memory actuator causes the pawl to pivot with respect to the force receiving member and bind on to the force receiving member substantially eliminating motion between the pawl and the force receiving member.

20. A drive mechanism in accordance with claim 19, wherein the force applying member is stationary and the force receiving member is moved by the force applying member.

21. A drive mechanism in accordance with claim 19, wherein the force receiving member remains stationary and the force applying member is moved relative to the force receiving member.

22. A drive mechanism in accordance with claim 19, wherein the force receiving member is a guide and the force applying member is a carriage assembly.

23. A drive mechanism in accordance with claim 19, wherein the shape memory actuator is heat activated by applying and removing an electric current to the shape memory actuator.

24. A drive mechanism in accordance with claim 23, wherein the shape memory actuator is formed from Nitinol material.

25. A drive mechanism in accordance with claim 19, wherein the drive mechanism utilizes less than three shape memory actuators.

26. A drive mechanism in accordance with claim 19, wherein the relative movement to between the force receiving member and the force applying member is translational movement.

* * * * *